United States Patent [19]
Warner et al.

[11] Patent Number: 5,731,252
[45] Date of Patent: Mar. 24, 1998

[54] PROCESS FOR IMPROVING PRODUCTIVITY OF A CARBONYLATION CATALYST SOLUTION BY REMOVING CORROSION METALS

[75] Inventors: R. Jay Warner; Jerry Allen Broussard, both of Corpus Christi, Tex.

[73] Assignee: Hoechst Celanese Corporation, Warren, N.J.

[21] Appl. No.: 786,016

[22] Filed: Jan. 21, 1997

Related U.S. Application Data

[63] Continuation of Ser. No. 549,609, Oct. 27, 1995, abandoned.
[51] Int. Cl.$^6$ .................................. B01J 37/30; B01J 38/48
[52] U.S. Cl. .................................. 502/22; 502/12; 562/519
[58] Field of Search .......................... 502/12, 22; 562/519

[56] References Cited

U.S. PATENT DOCUMENTS

| | | | |
|---|---|---|---|
| 3,769,329 | 10/1973 | Paulik et al. | 260/488 K |
| 4,007,130 | 2/1977 | Leach et al. | 252/411 R |
| 4,792,620 | 12/1988 | Paulik et al. | 560/232 |
| 4,894,477 | 1/1990 | Scates et al. | 562/519 |
| 5,001,259 | 3/1991 | Smith et al. | 562/519 |

FOREIGN PATENT DOCUMENTS 0 161 874 B2   1/1992   European Pat. Off.

OTHER PUBLICATIONS

Periodic Table of Elements, CRC Handbook of Chemistry and Physics, 76th Ed., New York (1995-96).

Primary Examiner—Walter D. Griffin
Assistant Examiner—Alexander G. Ghyka
Attorney, Agent, or Firm—M. Susan Sniering

[57] ABSTRACT

A process for treating low water content carbonylation catalyst solutions which contain a rhodium component and an alkali metal component to remove metallic corrosion products is disclosed. The process comprises contacting the catalyst solution with an ion exchange resin, preferably in the lithium form, and a sufficient amount of water to decrease the concentration of alkali metal ions to optimize removal of corrosion metal products.

15 Claims, 1 Drawing Sheet

PROCESS FOR IMPROVING PRODUCTIVITY OF A CARBONYLATION CATALYST SOLUTION BY REMOVING CORROSION METALS

This application is a continuation of application Ser. No. 08/549,609, filed Oct. 27, 1995, now abandoned.

FIELD OF THE INVENTION

This invention relates generally to an improvement in the process for carbonylating methanol to acetic acid in the presence of a rhodium-containing catalyst. More particularly, the invention relates to an improved process for regenerating a catalyst solution employed in a low water carbonylation reaction process.

BACKGROUND OF THE INVENTION

Among currently-employed processes for synthesizing acetic acid one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or supported on an inert solid, along with a halogen-containing catalyst promoter as exemplified by methyl iodide. The rhodium can be introduced into the reaction system in one of many forms, and it is not relevant, if indeed it is possible, to identify the exact nature of the rhodium moiety within the active catalyst complex. Likewise, the nature of the halide promoter is not critical. U.S. Pat. No. '329 discloses a number of suitable promoters, most of which are organic iodides. Most typically and usefully, the reaction is conducted with the catalyst being dissolved in a liquid reaction medium through which carbon monoxide gas is continuously bubbled.

An improvement in the prior-art process for the carbonylation of an alcohol to produce the carboxylic acid having one carbon atom more than the alcohol in the presence of a rhodium catalyst is disclosed in U.S. Pat. No. 5,001,259 and European patent 161,874 B2. As disclosed therein acetic acid (HAc) is produced from methanol (MeOH) in a reaction medium comprising methyl acetate (MeOAc), methyl halide, methyl iodide, (MeI), and rhodium present in a catalytically-effective concentration. The invention therein resides in the discovery that catalyst stability and the productivity of the carbonylation reactor can be maintained at surprisingly high levels, even at very low water concentrations, i.e. 4 wt % or less, in the reaction medium (despite the general industrial practice of maintaining approximately 14 wt % or 15 wt % water). As described in U.S. Pat. No. '259, the carbonylation reaction proceeds by maintaining in the reaction medium, a catalytically-effective amount of rhodium, at least a finite concentration of water, methyl acetate and methyl iodide, and a specified concentration of iodide ions over and above the iodide content which is present as methyl iodide or other organic iodide. The iodide ion is present as a salt, with lithium iodide being preferred. U.S. Pat. No. '259 and EP '874 teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %; so low that it can broadly be defined simply as 'a finite concentration' of water. Furthermore, the reaction medium employed improves the stability of the rhodium catalyst. This catalyst stability is improved by having a resistance to catalyst precipitation, especially during the product-recovery steps of the process wherein distillation for the purpose of recovering the acetic acid product tends to remove, from the catalyst, the carbon monoxide which in the environment maintained in the reaction vessel, is a ligand with stabilizing effect on the rhodium. U.S. Pat. No. 5,001,259 is herein incorporated by reference.

In operation of the process for the carbonylation of methanol to acetic acid on a continuous basis, a solution containing the soluble catalyst complex is separated from the reactor effluent and recycled to the reactor. However, with operation over extended periods of time, corrosion products dissolve from the vessels of the metallurgy stream, e.g., iron, nickel, molybdenum, chromium, and the like and build up in the catalyst recycle stream. Such foreign metals, if present in sufficient quantity are known to interfere with the carbonylation reaction or accelerate competing reactions such as the water-gas shift reaction (carbon dioxide and hydrogen formation) and methane formation. Thus, the presence of these corrosion metal contaminants have an adverse effect on the process, in particular, a consequent loss in yield based on carbon monoxide. Further, foreign metals can react with ionic iodine thus making this component of the catalytic system unavailable for reaction with rhodium and causing instability in the catalyst system. In view of the high cost of the rhodium-containing catalyst, replacement of spent catalyst can be effected only at a prohibitive cost. Consequently, a method for regeneration of the catalyst is not only desirable but necessary.

According to U.S. Pat. No. 4,007,130, a carbonylation catalyst solution comprising the complex reaction product of a rhodium component or an iridium component, a halogen component, and carbon monoxide which contains metallic corrosion products is intimately contacted with a ion exchange resin in its hydrogen form and the catalyst solution recovered free of the metallic corrosion products. As disclosed in U.S. Pat. No. '130, the contacting is effected by passing the catalyst solution containing the undesirable corrosion metal contaminants through a bed of the ion exchange resin and recovering as the effluent from the bed, the catalyst solution containing the complex rhodium or iridium component but substantially free of the corrosion products which are adsorbed on and removed by the resin bed. Upon exhaustion, as indicated by breakthrough of the corrosion metal products in the effluent, the resin bed is regenerated by treatment with a mineral acid such as hydrochloric, sulfuric, phosphoric or hydriodic acid and re-used.

However, U.S. Pat. No. '130 does not contemplate using the catalyst solutions such as set forth in the aforementioned U.S. Pat. No. 5,001,259. Thus, in the improved catalyst solutions as previously discussed, there is present a specified concentration of iodide ions over and above the iodide content which is present as methyl iodide or other organic iodide. This additional iodide ion is present as a salt, and most preferably, as lithium iodide. What has been discovered is that in regenerating the catalyst solution in order to remove the metal contaminants by means of passing the catalyst solution through a bed of a cation exchange resin in the hydrogen form as disclosed in U.S. Pat. No. 4,007,130, the alkali metal ion in the catalyst solution is preferably removed. The removal of the alkali metal ion from the catalyst solution greatly reduces the reactivity and stability of the reaction medium.

Accordingly, it is necessary to provide an improved process for regenerating carbonylation catalyst solutions which contain alkali metal ions, in particular lithium, to allow the removal of corrosion metal contaminants from the catalyst solutions and to avoid the removal of the desirable components from such solutions. It is therefore an object of the present invention to provide a process for treating carbonylation catalyst solutions containing lithium to remove metallic corrosion products therefrom and to recover the catalyst solution in a form suitable for return to the process as an active catalyst without the need for excessive replacement of the components therein.

U.S. Pat. No. 4,894,477, herein incorporated by reference, teaches the use of strongly acidic ion exchange resin in the lithium form to remove corrosion metals (e.g., iron, nickel, molybdenum, chromium, and the like) from the carbonylation reaction system. The process described in U.S. Pat. No. '477 is particularly applicable to those processes which are useful for the carbonylation of methanol to acetic acid under low water conditions, such as set forth in U.S. Pat. No. 5,001,259. Low water conditions improve the acetic acid purification/production process. However, as lithium concentrations in the low water conditions carbonylation reactor are increased to increase rhodium stability and as the water levels in the reaction system are decreased, the capacity of the ion exchange corrosion metal removal process per cycle is diminished. Alternatively stated, there is a greater tendency for corrosion metals to build up in the carbonylation catalyst solution in a low water process. The low water conditions makes it difficult to remove corrosion metals from the carbonylation reaction. This problem was not recognized at the time of filing U.S. Pat. No. '477. Accordingly, it is desirable to provide a process for treating the carbonylation catalyst solutions to remove metallic corrosion products from a low water condition carbonylation process.

SUMMARY OF THE INVENTION

The present invention relates to a process for regenerating or improving the productivity of a carbonylation catalyst solution under low water conditions. The catalyst solution contains soluble rhodium complexes and corrosion metal contaminants. The improved process comprises intimately contacting the catalyst solution with an ion exchange resin (IER) in the alkali metal form, preferably in the lithium form, and a sufficient amount of water to optimize removal of corrosion metals from the catalyst solution and, recover a catalyst solution of reduced metal contaminant content. The corrosion metal contaminants include iron, nickel, chromium, molybdenum, and the like.

Generally the catalyst solution has a water concentration of from about 5 to about 50 wt %, preferably about 5 to about 30 wt % and most preferably about 5 to about 15 wt % for improved corrosion metal removal.

In accordance with the present invention, a catalyst solution comprising rhodium and at least a finite concentration of alkali metal ions, preferably lithium ions, which is contaminated with corrosion metals and has a set water concentration is intimately contacted with an ion exchange resin wherein an additional quantity of water is added to the resin in an amount sufficient to increase the concentration of water (or decrease the concentration of the alkali metal ions) in the catalyst solution and a catalyst solution is recovered free or substantially reduced of the metallic contaminants.

Generally, the contacting is effected by passing the catalyst solution containing the undesirable metal contaminants through a bed of the ion exchange resin in the alkali metal form, preferably the Li form, and recovering as the effluent from the bed the catalyst solution containing the rhodium component and the lithium component, but substantially freed from the corrosion products which are removed by the resin bed. Upon exhaustion of the ion exchange resin, the resin bed can be regenerated by treatment with a lithium salt such as lithium acetate and reused. Sources of water for the ion exchange resin bed include but are not limited to fresh water added to the resin bed, or water from process streams throughout the reaction system wherein water may be the sole or primary component from the carbonylation reaction system.

The inventive process solves a problem associated with low water carbonylation reaction systems. It is disclosed herein with reference to a carbonylation process employing an ion exchange resin in its lithium form. However, the ion associated with the resin may be any known alkali metal cation, for example, lithium, sodium, potassium, and the like, provided that the corresponding ion is being employed as the iodide promoter in the reaction system.

DETAILED DESCRIPTION OF THE INVENTION

Figure 1:
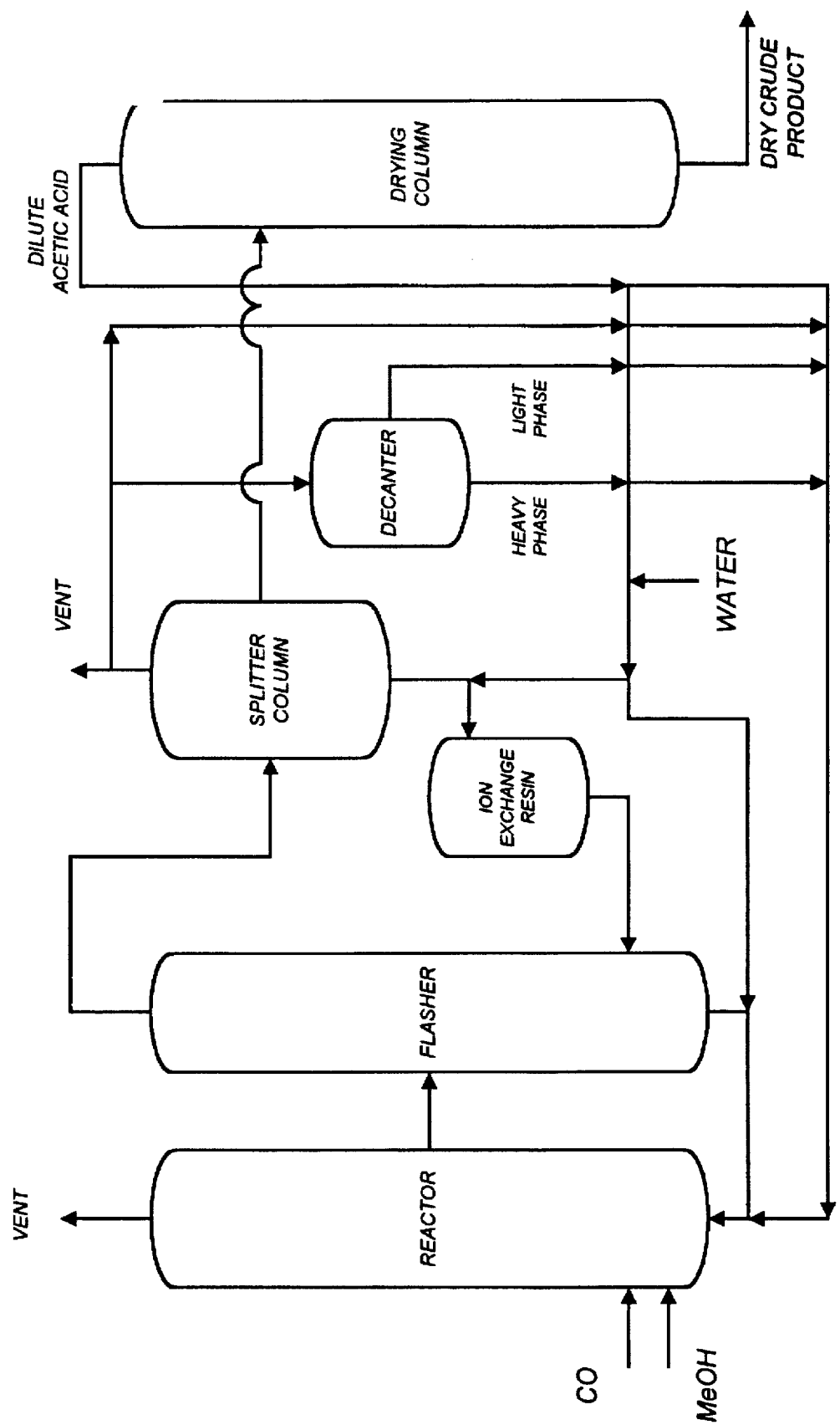
FIG. 1 is a schematic diagram illustrating the flow of process streams used in the catalytic carbonylation of methanol to acetic acid and the removal of metallic corrosion products from the process streams.

One embodiment of the present invention relates to an improvement in the process for the carbonylation of methanol to acetic acid in a carbonylation reactor by passing carbon monoxide and methanol to a reaction medium contained in a reactor and comprising an acetic acid solution of low water content containing rhodium, a methyl iodide promoter, methyl acetate, and lithium iodide. The product, acetic acid, is recovered from the effluent of the reactor by reducing the pressure of the solution to separate as a vapor, the product from the catalyst solution, which catalyst solution is then recycled to the reactor. During reaction and during the various processing steps, corrosion metals are dissolved from the vessels and towers and will appear in various processing streams. Thus these streams may contain the corrosion metal contaminants and are the streams to be contacted with a ion exchange resin to remove corrosion metal contaminants. The improvement of this invention comprises increasing the water content, preferably of the process streams, passing through the ion exchange resin, in an amount sufficient to optimize removal of corrosion metal contaminants and recovering a process stream of substantially reduced metal contaminant content.

Another embodiment of the present invention relates to a process for improving the productivity of a catalyst solution comprising a set water concentration, a set concentration of alkali metal ions, and corrosion metal contaminants selected from the group consisting of iron, nickel, chromium, molybdenum and mixtures thereof, which process comprises intimately contacting the catalyst solution with an ion exchange resin in the alkali metal form, preferably the lithium form, and an aqueous medium, preferably water, in an amount sufficient to decrease the concentration of metal ions in the catalyst solution and recovering a catalyst solution of reduced corrosion metal contaminant content.

The process of the present invention is applicable to the regeneration of, or improving the productivity of low water content catalyst solutions containing metal salts, soluble rhodium complexes, and metallic contaminants. The catalyst solutions to which the regeneration technique of the invention is particularly applicable are those which are useful for the carbonylation of methanol to acetic acid under low water conditions such as set out in U.S. Pat. No. 5,001,259. Thus, the catalyst solutions to be improved in accordance with the process of the present invention will preferably contain the rhodium catalyst and lithium ion which is present as a lithium iodide salt.

Although the present invention is directed and exemplified with respect to the production of acetic acid, the invention is equally applicable to processes for the production of other carbonylation products. For example, the present inventive technology may be applied to the production of acetic anhydride or the coproduction of acetic acid and acetic anhydride. Generally anhydrous conditions are employed for the carbonylation process for the production of acetic anhydride or the coproduction of acetic anhydride and acetic acid. In accordance with the present invention, for the production of acetic anhydride or the coproduction of acetic anhydride and acetic acid, an aqueous medium, preferably water, may be added to the ion exchange resin bed to improve the corrosion metal removal process and thus improve productivity of the catalyst solution. Other processes where the present invention may be employed include the carbonylation of alcohols, esters, or ethers to their corresponding acids, anhydrides, or mixtures thereof. Generally these alcohols, esters, or ethers contain from 1 to about 20 carbon atoms.

In the low water carbonylation of methanol to acetic acid as exemplified in U.S. Pat. No. 5,001,259, the catalyst which is employed includes a rhodium component and a halogen promoter in which the halogen is either bromine or iodine, or bromide or iodide compounds. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing into the reaction zone rhodium in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

Water is also added to the reaction medium, but at concentrations well below what has heretofore been thought practical for achieving sufficient reaction rates. It is known that in rhodium-catalyzed carbonylation reactions, the addition of water exerts a beneficial effect upon the reaction rate (U.S. Pat. No. 3,769,329). Thus, commercial operations run at water concentrations of at least 14 wt %. According to U.S. Pat. No. '259, it is quite unexpected that reaction rates substantially equal to and above reaction rates obtained with such high levels of water concentration can be achieved with water concentrations below 14 wt % and as low as 0.1 wt. %.

In accordance with the carbonylation process described in U.S. Pat. No. '477, the desired reaction rates are obtained even at low water concentrations by including in the reaction medium an ester which corresponds to the alcohol being carbonylated and the acid product of the carbonylation reaction and an additional iodide ion which is over and above the iodide which is present as a catalyst promoter such as methyl iodide or other organic iodide. Thus, in the carbonylation of methanol to acetic acid, the ester is methyl acetate and the additional iodide promoter is an iodide salt, e.g., lithium iodide. It has been found that under low water concentrations, methyl acetate and lithium iodide act as rate promoters only when relatively high concentrations of each of these components are present and that the promotion is higher when both of these components are present simultaneously. This had not been recognized earlier. The concentration of lithium iodide used in the reaction medium described in U.S. Pat. No. '477 is believed to be quite high as compared with what little prior art there is dealing with the use of halide salts in reaction systems of this sort.

As mentioned above, the low water carbonylation catalyst solutions are useful in carbonylating alcohols. Useful feedstocks which can be carbonylated include alkanols having 1–20 carbon atoms. Preferred feedstocks are alkanols containing 1–10 carbon atoms, and more preferred are alkanols of 1–6 carbon atoms. Methanol is the particularly preferred feed and is converted to acetic acid.

The carbonylation reaction may be carried out by intimately contacting the defined feed alcohol, which is in the liquid phase, with gaseous carbon monoxide bubbled through a liquid reaction medium containing the rhodium catalyst, halogen-containing promoting component, alkyl ester, and additional soluble iodide salt promoter, at conditions of temperature and pressure suitable to form the carbonylation product. Thus, if the feed is methanol, the halogen-containing promoting component will comprise methyl iodide and the alkyl ester will comprise methyl acetate. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation can be used provided that the salt is sufficiently soluble in the reaction medium to provide the desired level of the iodide. The iodide salt can be a quaternary salt of an organic cation or the iodide salt of an inorganic cation, preferably it is an iodide salt of a member of the group consisting of the metals of Group 1 and 2 of the periodic table (as set forth in the "Handbook of Chemistry and Physics, published by CRC Press, Cleveland, Ohio, 1995–96 (76th edition)). In particular, alkali metal iodides are useful, with lithium iodide being preferred. It is, however, the use of lithium iodide and the inadvertent loss thereof during removal of metal contaminants from catalyst solutions by ion exchange which is the problem directly solved by the catalyst regeneration process of this invention.

Typical reaction temperatures for carbonylation will be approximately 150°–250° C., with the temperature range of about 180°–220° C. being the preferred range. The carbon monoxide partial pressure in the reactor can vary widely but is typically about 2–30 atmospheres, and preferably, about 4–15 atmospheres. Because of the partial pressure of byproducts and the vapor pressure of the contained liquids, the total reactor pressure will range from about 15 to 40 atmospheres.

FIG. 1 illustrates a reaction system which can be employed, in the catalyst regeneration process of the present invention. The reaction system comprises a liquid-phase carbonylation reactor, a flasher, a methyl iodide-acetic acid splitter column (hereinafter splitter column), a decanter, a drying column, and an ion exchange resin. For purposes of illustration, one IER is shown in FIG. 1. It is understood that the carbonylation process may have greater than one IER bed available for use. The carbonylation reactor is typically a stirred autoclave within which the reacting liquid contents are maintained automatically at a constant level. Into this reactor there is continuously introduced carbon monoxide, fresh methanol, sufficient water to maintain at least a finite concentration of water in the reaction medium, recycled catalyst solution from the flasher base and recycled methyl iodide and methyl acetate from the overhead of the splitter column. Alternate distillation systems can be employed so long as they provide means for recovering the crude acetic acid and recycling to the reactor catalyst solution, methyl iodide, and methyl acetate. In the preferred process, carbon monoxide feed is continuously introduced into the carbonylation reactor just below the agitator. The gaseous feed is thoroughly dispersed through the reacting liquid by mixing. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from the carbonylation reactor at a rate sufficient to maintain a constant level therein and is introduced to the flasher at a point intermediate between the top and bottom thereof. In the flasher, the catalyst solution is withdrawn as a base stream (predominantly acetic acid containing the rhodium and the iodide salt along with lesser quantities of methyl acetate, methyl iodide, and water), while the overhead of the flasher comprises largely the product acetic acid along with methyl iodide, methyl acetate, and water. A portion of the carbon monoxide along with gaseous by-products such as methane, hydrogen, and carbon dioxide exit the top of the flasher.

The product acetic acid drawn from the base of the splitter column (it can also be withdrawn as a side stream) is then drawn off for final purification as desired by methods which are obvious to those skilled in the art and which are outside the scope of the present invention. Use of a drying column is one means of purification of acetic acid product. The overhead from the splitter column, comprising mainly methyl iodide and methyl acetate, is recycled to the carbonylation reactor along with fresh methyl iodide; the fresh methyl iodide being introduced at a rate sufficient to maintain in the carbonylation reactor the desired concentration of methyl iodide in the liquid reaction medium. The fresh methyl iodide is needed to compensate for small losses of methyl iodide in the flasher and carbonylation reactor vent streams. A portion of the overhead from the splitter column is introduced into a decanter which partitions the methyl iodide and methyl acetate streams into a heavy phase of aqueous methyl iodide and methyl acetate and a light phase comprising aqueous acetic acid. Any water from the purification stage which will contain small amounts of acetic acid can be combined with the light aqueous acetic acid phase from the decanter for return to the reactor.

It has been found that metal contaminants, in particular, iron, nickel, chromium and molybdenum can be present in any of the process streams as previously described. The accumulation of these metal contaminants has an adverse effect on the rate at which acetic acid is produced and the stability of the process, in general. Accordingly, an ion exchange resin is placed within the processing scheme to remove these metal contaminants from the processing streams. In FIG. 1, an ion exchange resin is employed to remove corrosion metal contaminants from the catalyst solution recycled from the base of the flasher to the reactor. It should be understood, that any of the process streams can be treated with the ion exchange resin to remove metal contaminants therefrom. The only criteria necessary is that the processing stream be at a temperature which does not deactivate the resin. Generally, the processing streams which are treated will have a finite concentration of the rhodium catalyst and/or lithium cation from the additional lithium iodide salt which is added as a catalyst promoter. In FIG. 1, the stream from the base of the splitter column is treated to remove corrosion metals, and water is directed from the dilute acetic acid stream to the ion exchange resin.

Sources for the water to add to the resin include fresh water from outside of the reaction system, or water from within the reaction system which is ultimately returned to the reactor. It is preferred that water from within the reaction system be directed to the resin for use in the improved corrosion metal removal process. A water balance then remains within the carbonylation reaction system. Examples of water sources include (but are not limited to) water contained in the recycle dilute acetic acid streams, water from the light phase, or water from combined streams (for example the combined heavy and light phase streams, or combined light phase and dilute acetic acid streams) which together may have a high concentration of water present. Water may be employed from any point within the reaction system.

The addition of water to the ion exchange resin can be varied to optimize corrosion metal removal. At carbonylation reactor conditions employing 14 wt % or 15 wt % water, only small improvements in the amount of corrosion metal removal per ion exchange resin exhaustion cycle would be expected. However, under low water carbonylation reactor conditions the necessity for proper water concentration in the IER corrosion removal process is significant. Generally, the water content in the catalyst solution is from about 5 to about 50 wt %. However a preferred range is from about 5 to about 30 wt % and a more preferred range is from about 5 to about 15 wt %.

The resins useful for regenerating the catalyst solutions according to the present invention are cation exchange resins either of the strong-acid or the weak-acid type. As mentioned previously, any cation is acceptable provided the corresponding cation is employed in the iodide promoter. For purposes of illustrating the present invention, a cation exchange resin in its lithium form is employed. Both strong- and weak-acid type resins are readily available as commercial products. The weak-acid cation exchange resins are mostly copolymers of acrylic or methacrylic acids or esters or the corresponding nitriles, but a few of those marketed are phenolic resins. Strong-acid cation exchange resins, which are the resins preferred for use in the present invention, are constituted predominantly of sulfonated styrene-divinylbenzene copolymers although some of the available resins of this type are phenol-formaldehyde condensation polymers. Either the gel type or the macroreticular type resin is suitable but the latter is preferred since organic components are present in the catalyst solutions being treated.

Macroreticular resins are commonly employed in the catalytic art. They requires minimal water to maintain their swelling properties. The present invention is particularly surprising since it is believed by those of skill in the art that with use of macroreticular type resin, very little water is necessary for their use. As such, problems were not anticipated with the resin when the carbonylation process was changed from a high water to a low water process. However, here, it was found that as water concentration was decreased in the reaction process, so was the ability to remove corrosion metals in the presence of a high lithium ion concentration using a macroreticular resin.

Contacting of the metal-contaminated catalyst solutions and the resin can be effected in a stirred vessel wherein the resin is slurried with the catalyst solution with good agitation and the catalyst solution is then recovered by decantation, filtration, centrifuging, etc. However, treatment of the catalyst solutions is usually effected by passing the metal contaminated solution through a fixed-bed column of the resin. The catalyst regeneration can be carried out as a batch, semi-continuous or continuous operation either with manual or automatic control employing methods and techniques well known in the art of ion-exchange.

The ion exchange treatment can be effected at temperatures in the range from about 0° to about 120° C., although lower or higher temperatures are limited only by the stability of the resin to be employed. Preferred temperatures are those in the range from about 20° C. to about 90° C.; chromium removal is more efficient at the higher temperatures. At the higher temperatures, a nitrogen or CO purge is desirable. If temperatures above the boiling point of the catalyst solutions are employed, then operation under pressure will be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of the catalyst solution through the resin during the corrosion metal removal process will, in general, be that recommended by the resin manufacturer and will usually be from about 1 to about 20 bed volumes per hour. Preferably, the flow rates will be from about 1 to about 12 bed volumes per hour. After contacting the bed with rhodium containing process streams, washing or rinsing of the resin bed with water or the carbonylation product from the process from which the catalyst being treated is derived, such as acetic acid, is essential for removing all the rhodium from the resin bed. The rinsing or washing is effected at similar flow rates as in the removal step.

After the resin has become exhausted, i.e., when the metal contaminants are breaking through into the effluent, the resin can be regenerated by passing therethrough a solution of organic salts; for illustrative purposes, preferably lithium salts. Generally, the lithium salt used in the regenerating cycle has a concentration in the range from about 1 wt % to about 20 wt %. Quantities employed and procedures are those well established in the art and recommended by the resin manufacturers. Aqueous lithium acetate is preferred as a regenerating agent since the acetate anion is employed in the reaction system and is readily available for use. A further advantage is that its use eliminates the rinsing step normally required after the regeneration process when other regenerates are employed.

To maximize corrosion metal regeneration capacity and to maximize resin bed column performance at relatively high concentrations of lithium acetate, the lithium acetate regeneration solution should contain some acetic acid, or product being produced, to avoid the formation of any insoluble corrosion metal compounds during the regeneration cycle. Precipitation of these compounds during the regeneration cycle could reduce the regeneration performance of the column and also cause plugging of the resin bed. Typically, acetic acid concentrations of from about 0.1 to about 95 wt % can be used, with acetic acid concentrations of from about about 0.1 to 20 wt % being preferred.

The treatment of the catalyst solution can be operated as a batch or a continuous operation. The preferred type of operation is continuous. In a continuous process, a slip stream from a catalyst solution being recycled to the reactor for producing the acids, is withdrawn, passed through the ion exchange resin bed, along with an aqueous recycle stream to provide sufficient water concentration to enhance the amount of the corrosion products being adsorbed thereon, and the effluent, free of said corrosion products, along with the combined aqueous recycle material is returned to the catalyst recycle stream and hence to the reactor. The ion-exchange operation can be cyclic (wherein greater than one resin is available for use). As the resin becomes exhausted in one resin bed, the slip stream of catalyst solution can be diverted to a fresh bed while the exhausted bed is subjected to regeneration.

The invention is further illustrated by the following non-limiting examples.

EXAMPLES

TABLE 1

Comparison of corrosion metal removal from catalyst solution* at various water concentrations (Li/Fe molar ratio in catalyst solution approx. 86+/−5:1)

| Example | Water, Wt. % | Fe removal, g/L IER |
|---------|--------------|---------------------|
| 1 | 1.23 | 0.09 |
| 2 | 6.4 | 0.36 |
| 3 | 10.96 | 0.93 |
| 4 | 15.1 | 1.85 |
| 5 | 46.0 | 6.9 |

*Catalyst solution was obtained from the flasher residue. The exhaustive cycle was run
down flow at a feed rate (typically at 1–2 bed volume per hour) through 100 ml Rohm &
Haas, Amberlyst-15 (A-15) macroreticular strongly acidic ion exchange resin in the Li form
followed by a rinse step and regeneration of the IER bed using 10 wt% LiAc aqueous
solution typically containing about 10 wt% acetic acid.

TABLE 2

Comparison of corrosion metal removal from a synthetic catalyst solution** at various water concentrations. (Li/Fe molar ratio in catalyst solution approx. 54:1)

| Example | Water, Wt. % | Fe removal, g/L IER |
|---------|--------------|---------------------|
| 6 | 0.27 | 0.456 |
| 7 | 1.70 | 0.471 |
| 8 | 5.34 | 1.325 |
| 9 | 10.62 | 2.760 |
| 10 | 14.81 | 3.137 |
| 11 | 19.02 | 3.341 |
| 12 | 34.45 | 3.673 |
| 13 | 47.36 | 3.940 |

**A series of batch experiments were conducted each with approximately
13.3 ml A-15 IER,
80 g of acetic acid solution containing approx. 973 ppm Fe and approx. 6502 ppm Li with
various additions of water. Samples were analyzed after 13 and 29.5 hours to establish
equilibrium. The results of examples 6–13 show a trend similar to that illustrated by catalyst
runs of examples 1–5.

I claim:

1. A process for improving the productivity of a carbonylation catalyst solution employed under low water conditions, said carbonylation catalyst solution containing corrosion metal contaminants, which process comprises contacting the carbonylation catalyst solution with an ion exchange resin and water in an amount sufficient to bring the water concentration of the catalyst solution as it proceeds through the contacting cycle within a range of about 0.25 wt. % to about 50 wt. % and, recover a catalyst solution of reduced corrosion metal contaminant content.

2. The process of claim 1 wherein the resin is a strong-acid cation exchange resin.

3. The process of claim 1 wherein said contacting is effected by passing the catalyst solution through a fixed-bed column of said resin.

4. The process of claim 1 wherein said resin is regenerated after exhaustion by washing with a alkali metal salt.

5. The process of claim 4 wherein said alkali metal salt is lithium acetate.

6. The process of claim 4 wherein the alkali metal is potassium.

7. The process of claim 4 wherein the alkali metal is sodium.

8. A process for improving the productivity a catalyst solution comprising a set water and alkali metal ion concentration and corrosion metal contaminants selected from the group consisting of iron, nickel, chromium, molybdenum and mixtures thereof, which process comprises contacting said catalyst solution in a contacting cycle with a cation exchange resin and water in an amount sufficient to bring the water concentration of the catalyst solution as it proceeds through the contacting cycle within a range of about 0–2.5 wt. % to about 50 wt. %.

9. A process for improving the productivity of a carbonylation catalyst solution employed under low water conditions, said solution containing rhodium and alkali metal and further containing corrosion metal contaminants, which process comprises contacting the catalyst solution with an ion exchange resin and water in an amount sufficient to bring the water concentration of the catalyst solution as it proceeds through the contacting cycle within a range of about 0.25 wt. % to about 50 wt. % and, recover a catalyst solution of reduced corrosion metal contaminant content.

10. The process of claim 1 wherein the water concentration of the catalyst solution as it proceeds through the contacting cycle is within a range of about 5 wt. % to about 30 wt. %.

11. The process of claim 10 wherein the water concentration of the catalyst solution as it proceeds through the contacting cycle is within a range of about 5 wt. % to about 15 wt. %.

12. The process of claim 8 wherein the water concentration of the catalyst solution as it proceeds through the contacting cycle is within a range of about 5 wt. % to about 30 wt. %.

13. The process of claim 12 wherein the water concentration of the catalyst solution as it proceeds through the contacting cycle is within a range of about 5 wt. % to about 15 wt. %.

14. The process of claim 9 wherein the water concentration of the catalyst solution as it proceeds through the contacting cycle is within a range of about 5 wt. % to about 30 wt. %.

15. The process of claim 14 wherein the water concentration of the catalyst solution as it proceeds through the contacting cycle is within a range of about 5 wt. % to about 15 wt. %.

* * * * *